(12) United States Patent
Adler et al.

(10) Patent No.: US 7,241,262 B2
(45) Date of Patent: Jul. 10, 2007

(54) IMAGE-DISTORTING ENDOSCOPES AND METHODS OF MAKING AND USING SUCH ENDOSCOPE

(75) Inventors: Doron Adler, Nesher (IL); Ofer Pillar, Haifa (IL); Alex Zaretski, Nesher (IL); Arie Blumenzweig, Netanya (IL)

(73) Assignee: C2Cure, Inc., Wilmington, DE (US)

( * ) Notice: Subject to any disclaimer, the term of this patent is extended or adjusted under 35 U.S.C. 154(b) by 288 days.

(21) Appl. No.: 10/683,344

(22) Filed: Oct. 14, 2003

(65) Prior Publication Data
US 2004/0082833 A1 Apr. 29, 2004

Related U.S. Application Data

(62) Division of application No. 09/826,163, filed on Apr. 5, 2001, now Pat. No. 6,659,940.

(30) Foreign Application Priority Data
Apr. 10, 2000 (IL) ..................... 135571

(51) Int. Cl.
*A61B 1/05* (2006.01)
(52) U.S. Cl. ............ 600/130; 600/109; 600/111; 600/166; 600/176
(58) Field of Classification Search ........ 600/109, 600/111, 166, 176, 129, 130, 178; 348/65, 348/76, 340; 359/668
See application file for complete search history.

(56) References Cited

U.S. PATENT DOCUMENTS

| | | | |
|---|---|---|---|
| 3,971,065 A | | 7/1976 | Bayer |
| 4,253,447 A | * | 3/1981 | Moore et al. ............. 600/109 |
| 4,467,361 A | * | 8/1984 | Ohno et al. ............. 348/340 |
| 4,491,865 A | | 1/1985 | Danna et al. |
| 4,555,768 A | | 11/1985 | Lewis, Jr. et al. |
| 4,569,335 A | | 2/1986 | Tsuno |
| 4,576,146 A | | 3/1986 | Kawazoe et al. |
| 4,604,992 A | | 8/1986 | Sato |
| 4,646,721 A | | 3/1987 | Arakawa |
| 4,651,201 A | | 3/1987 | Schoolman |
| 4,682,219 A | | 7/1987 | Arakawa |
| 4,692,608 A | | 9/1987 | Cooper et al. |
| 4,697,208 A | | 9/1987 | Eino |

(Continued)

FOREIGN PATENT DOCUMENTS

WO  WO9732534 A1  9/1997

(Continued)

OTHER PUBLICATIONS

European Examination Report for European Application No. 01919745.8, dated Jul. 20, 2006; EPO, 4 pages.

(Continued)

*Primary Examiner*—John P. Leubecker
(74) *Attorney, Agent, or Firm*—Ganz Law, P.C.

(57) ABSTRACT

An endoscope having restricted dimensions and comprising at least one image gatherer, at least one image distorter and at least one image sensor shaped to fit within said limited dimensions, and wherein said image distorter is operable to distort an image received from said image gatherer so that the image is sensible at said shaped image sensor.

84 Claims, 10 Drawing Sheets

U.S. PATENT DOCUMENTS

| | | | |
|---|---|---|---|
| 4,720,178 A | | 1/1988 | Nishioka et al. |
| 4,746,203 A | | 5/1988 | Nishioka et al. |
| 4,784,133 A | | 11/1988 | Mackin |
| 4,803,562 A | | 2/1989 | Eino |
| 4,809,680 A | | 3/1989 | Yabe |
| 4,819,065 A | | 4/1989 | Eino |
| 4,827,907 A | | 5/1989 | Tashiro |
| 4,832,003 A | | 5/1989 | Yabe |
| 4,857,724 A | * | 8/1989 | Snoeren ............... 250/214 VT |
| 4,869,256 A | | 9/1989 | Kanno et al. |
| 4,934,339 A | | 6/1990 | Kato |
| 4,953,539 A | | 9/1990 | Nakamura et al. |
| 4,967,269 A | | 10/1990 | Sasagawa et al. |
| 4,986,642 A | * | 1/1991 | Yokota et al. ............. 359/708 |
| 5,010,875 A | | 4/1991 | Kato |
| 5,022,399 A | | 6/1991 | Biegeleisen |
| 5,029,574 A | | 7/1991 | Shimamura et al. |
| 5,122,650 A | | 6/1992 | McKinley |
| 5,166,787 A | | 11/1992 | Irion |
| 5,184,223 A | * | 2/1993 | Mihara ................. 348/207.99 |
| 5,216,512 A | * | 6/1993 | Bruijns et al. ............. 348/335 |
| 5,311,600 A | | 5/1994 | Aghajan et al. |
| 5,323,233 A | | 6/1994 | Yamagami et al. |
| 5,325,847 A | | 7/1994 | Matsuno |
| 5,335,662 A | | 8/1994 | Kimura et al. |
| 5,343,254 A | | 8/1994 | Wada et al. |
| 5,432,543 A | | 7/1995 | Hasegawa et al. |
| 5,444,574 A | * | 8/1995 | Ono et al. ................. 359/708 |
| 5,450,243 A | * | 9/1995 | Nishioka .................... 359/710 |
| 5,494,483 A | * | 2/1996 | Adair ........................ 600/111 |
| 5,498,230 A | | 3/1996 | Adair |
| 5,512,940 A | | 4/1996 | Takasugi et al. |
| 5,547,455 A | * | 8/1996 | McKenna et al. .......... 600/113 |
| 5,575,754 A | | 11/1996 | Konomura |
| 5,594,497 A | | 1/1997 | Ahern et al. |
| 5,598,205 A | * | 1/1997 | Nishioka .................... 348/65 |
| 5,603,687 A | * | 2/1997 | Hori et al. ................. 600/166 |
| 5,673,147 A | | 9/1997 | McKinley |
| 5,700,236 A | | 12/1997 | Sauer et al. |
| 5,728,044 A | | 3/1998 | Shan |
| 5,751,341 A | | 5/1998 | Chaleki et al. |
| 5,792,045 A | | 8/1998 | Adair |
| 5,797,837 A | | 8/1998 | Minami |
| 5,905,597 A | * | 5/1999 | Mizouchi et al. .......... 359/671 |
| 5,928,137 A | | 7/1999 | Green |
| 5,929,901 A | | 7/1999 | Adair et al. |
| 5,940,126 A | * | 8/1999 | Kimura ...................... 348/294 |
| 5,984,860 A | | 11/1999 | Shan |
| 5,986,693 A | | 11/1999 | Adair et al. |
| 6,009,189 A | | 12/1999 | Schaack |
| 6,010,449 A | | 1/2000 | Selmon et al. |
| 6,039,693 A | | 3/2000 | Seward et al. |
| 6,043,839 A | | 3/2000 | Adair et al. |
| 6,099,475 A | | 8/2000 | Seward et al. |
| 6,129,672 A | | 10/2000 | Seward et al. |
| 6,134,003 A | | 10/2000 | Tearney et al. |
| 6,142,930 A | * | 11/2000 | Ito et al. ..................... 600/109 |
| 6,148,227 A | | 11/2000 | Wagnieres et al. |
| 6,184,923 B1 | | 2/2001 | Miyazaki |
| 6,206,825 B1 | * | 3/2001 | Tsuyuki ...................... 600/182 |
| 6,281,506 B1 | * | 8/2001 | Fujita et al. ............ 250/370.09 |
| 6,416,463 B1 | | 7/2002 | Tsuzuki et al. |
| 6,476,851 B1 | | 11/2002 | Nakamura |
| 6,485,414 B1 | | 11/2002 | Neuberger |
| 6,533,722 B2 | | 3/2003 | Nakashima |
| 6,670,636 B2 | | 12/2003 | Hayashi et al. |
| 6,692,430 B2 | | 2/2004 | Adler |
| 2001/0031912 A1 | | 10/2001 | Adler |
| 2001/0040211 A1 | * | 11/2001 | Nagaoka ................... 250/241.1 |
| 2001/0051766 A1 | | 12/2001 | Gazdzinski |
| 2003/0174409 A1 | * | 9/2003 | Nagaoka ..................... 359/654 |
| 2004/0019255 A1 | | 1/2004 | Sakiyama |
| 2005/0259487 A1 | | 11/2005 | Glukhovsky et al. |

FOREIGN PATENT DOCUMENTS

| | | |
|---|---|---|
| WO | WO99/23812 | 5/1999 |
| WO | WO99/60916 A2 | 12/1999 |
| WO | WO/01/76452 | 10/2001 |
| WO | WO03/098913 A2 | 11/2003 |
| WO | WO03/098913 A3 | 11/2003 |

OTHER PUBLICATIONS

PCT International Search Report dated Oct. 11, 2001 for corresponding PCT International Application No. PCT/IL01/00313, filed Apr. 4, 2001, 3 pages.

PCT International Search Report for International Patent Application No. PCT/IL02/00999, dated Mar. 20, 2003 by ISA/US, 1 page.

PCT International Search Report for International Patent Application No. PCT/IL02/00399, dated Feb. 27, 2004 by ISA/US, 2 pages.

Cheong, et al. A Review of the Optical Properties of Biological Tissues, IEEE J. of Quantum Electronics, vol. 26, Dec. 12, 1990.

Roggan, Andre; Optical Properties of Circulating Human Blood in Wavelength Range 400-2500 nm; Journal of Biomedical Optics, Jan. 1999.

Zebra Elasticomeric Connectors, available at: http://www/fujipoly.com/products/genProductLine.asp?ProductLine=Zebra, Nov. 2004, 3 pages.

http://www/fujipoly.com/general/default.asp. Nov. 2004, 2 pages.

United States Patent and Trademark Office Action for U.S. Appl. No. 10/759,045 dated Aug. 9, 2006, 8 pages.

* cited by examiner

| R | G | R | G |  | ... |  | G |
|---|---|---|---|---|---|---|---|
| B | IR | B | IR |  | ... |  | IR |
| R | G | R | G |  | ... |  | G |
| B | IR | B | IR |  | ... |  | IR |
| . | . | . | . |  |  |  |  |
| . | . | . | . |  |  |  |  |
| . | . | . | . |  |  |  |  |
| B | IR | B | IR |  | ... |  | IR |

IMAGE-DISTORTING ENDOSCOPES AND METHODS OF MAKING AND USING SUCH ENDOSCOPE

RELATED PATENT APPLICATIONS

This application is a Divisional Patent Application of U.S. Application Ser. No. 09/826,163 filed Apr. 5, 2001, now U.S. Pat. No. 6,659,940, which claims priority from Israel Patent Application No. 135571 filed Apr. 10, 2000.

FIELD OF THE INVENTION

The present invention relates to an image sensor, and more particularly but not exclusively to two and three-dimensional optical processing from within restricted spaces, and an endoscope using the same.

BACKGROUND OF THE INVENTION

Endoscopy is a surgical technique that involves the use of an endoscope, to see images of the body's internal structures through very small incisions.

Endoscopic surgery has been used for decades in a number of different procedures, including gall bladder removal, tubal ligation, and knee surgery, and recently in plastic surgery including both cosmetic and re-constructive procedures.

An endoscope may be a rigid or flexible endoscope which consists of five basic parts: a tubular probe, a small camera head, a camera control unit, a bright light source and a cable set which may include a fiber optic cable. The endoscope is inserted through a small incision; and connected to a viewing screen which magnifies the transmitted images of the body's internal structures.

During surgery, the surgeon is able to view the surgical area by watching the screen while moving the tube of the endoscope through the surgical area.

In a typical surgical procedure using an endoscope, only a few small incisions, each less than one inch long, are needed to insert the endoscope probe and other instruments. For some procedures, such as breast augmentation, only two incisions may be necessary. For others, such as a forehead lift, three or four short incisions may be needed. The tiny eye of the endoscope camera allows a surgeon to view the surgical site.

An advantage of the shorter incisions possible when using an endoscope is reduced damage to the patient's body from the surgery. In particular, the risk of sensory loss from nerve damage is decreased. However, most current endoscopes provide only flat, two-dimensional images which are not always sufficient for the requirements of the surgery. The ability of an endoscope to provide three-dimensional information in its output would extend the field of endoscope use within surgery.

The need for a 3D imaging ability within an endoscope has been addressed in the past. A number of solutions that provide stereoscopic images by using two different optical paths are disclosed in Patents U.S. Pat. Nos. 5,944,655, 5,222,477, 4,651,201, 5,191,203, 5,122,650, 5,471,237, JP7163517A, U.S. Pat. Nos. 5,673,147, 6,139,490, 5,603,687, WO9960916A2, and JP63244011A.

Another method, represented by U.S. Patents, U.S. Pat. Nos. 5,728,044 and 5,575,754 makes use of an additional sensor that provides location measurements of image points. Patent JP8220448A discloses a stereoscopic adapter for a one-eye endoscope, which uses an optical assembly to divide and deflect the image to two sensors. A further method, disclosed in U.S. Pat. No. 6,009,189 uses image acquisition from different directions using one or more cameras. An attempt to obtain 3D information using two light sources was disclosed in U.S. Pat. No. 4,714,319 in which two light sources are used to give an illusion of a stereoscopic image based upon shadows. JP131622A discloses a method for achieving the illusion of a stereoscopic image by using two light sources, which are turned on alternately.

An additional problem with current endoscopes is the issue of lighting of the subject for imaging. The interior spaces of the body have to be illuminated in order to be imaged and thus the endoscope generally includes an illumination source. Different parts of the field to be illuminated are at different distances from the illumination source and relative reflection ratios depend strongly on relative distances to the illumination source. The relative distances however may be very large In a typical surgical field of view, distances can easily range between 2 and 20 cm giving a distance ratio of 1:10. The corresponding brightness ratio may then be 1:100, causing blinding and making the more distant object all but invisible.

One reference, JP61018915A, suggests solving the problem of uneven lighting by using a liquid-crystal shutter element to reduce the transmitted light. Other citations that discuss general regulation of illumination levels include U.S. Pat. No. 4,967,269, JP4236934A, JP8114755A and JP8024219A.

In general it is desirable to reduce endoscope size and at the same time to improve image quality. Furthermore, it is desirable to produce a disposable endoscope, thus avoiding any need for sterilization, it being appreciated that sterilization of a complex electronic item such as an endoscope being awkward in itself.

Efforts to design new head architecture have mainly concentrated on integration of the sensor, typically a CCD based sensor, with optics at the distal end. Examples of such integration are disclosed in U.S. Pat. Nos. 4,604,992, 4,491,865, 4,692,608, JP60258515A, U.S. Pat. Nos. 4,746,203, 4,720,178, 5,166,787, 4,803,562, 5,594,497 and EP434793B1. Reducing the overall dimensions of the distal end of the endoscope are addressed in U.S. Pat. Nos. 5,376,960 and 4,819,065, and Japanese Patent Applications No. 7318815A and No. 70221A. Integration of the endoscope with other forms of imaging such as ultrasound and Optical Coherence Tomography are disclosed in U.S. Pat. Nos. 4,869,256, 6,129,672, 6,099,475, 6,039,693, 55,022,399, 6,134,003 and 6,010,449

Intra-vascular applications are disclosed in certain of the above-mentioned patents, which integrate the endoscope with an ultrasound sensor or other data acquisition devices. Patents that disclose methods for enabling visibility within opaque fluids are U.S. Pat. Nos. 4,576,146, 4,827,907, 5,010,875, 4,934,339, 6,178,346 and 4,998,972.

Sterilization issues of different devices including endoscopes are discussed in WO9732534A1, U.S. Pat. Nos. 5,792,045 and 5,498,230. In particular JP3264043A discloses a sleeve that was developed in order to overcome the need to sterilize the endoscope.

The above-mentioned solutions are however incomplete and are difficult to integrate into a single endoscope optimized for all the above issues.

SUMMARY OF THE INVENTION

It is an aim of the present embodiments to provide solutions to the above issues that can be integrated into a single endoscope.

It is an aim of the embodiments to provide an endoscope that is smaller than current endoscopes but without any corresponding reduction in optical processing ability.

It is a further aim of the present embodiments to provide a 3D imaging facility that can be incorporated into a reduced size endoscope.

It is a further aim of the present embodiments to provide object illumination that is not subject to high contrast problems, for example by individual controlling of the light sources.

It is a further aim of the present embodiments to provide a modified endoscope that is simple and cost effective to manufacture and may therefore be treated as a disposable item.

Embodiments of the present invention provide 3D imaging of an object based upon photometry measurements of reflected light intensity. Such a method is relatively efficient and accurate and can be implemented within the restricted dimensions of an endoscope.

According to a first aspect of the present invention there is thus provided a pixilated image sensor for insertion within a restricted space, the sensor comprising a plurality of pixels arranged in a selected image distortion pattern, said image distortion pattern being selected to project an image larger than said restricted space to within said restricted space substantially with retention of an image resolution level.

Preferably, the image distortion pattern is a splitting of said image into two parts and wherein said pixilated image sensor comprises said pixels arranged in two discontinuous parts.

Preferably, the discontinuous parts are arranged in successive lengths.

Preferably, the restricted space is an interior longitudinal wall of an endoscope and wherein said discontinuous parts are arranged on successive lengths of said interior longitudinal wall.

Preferably, the restricted space is an interior longitudinal wall of an endoscope and wherein said discontinuous parts are arranged on successive lengths of said interior longitudinal wall.

Preferably, the distortion pattern is an astigmatic image distortion.

Preferably, the distortion pattern is a projection of an image into a rectangular shape having dimensions predetermined to fit within said restricted space.

A preferred embodiment includes one of a group comprising CMOS-based pixel sensors and CCD based pixel sensors.

A preferred embodiment is controllable to co-operate with alternating image illumination sources to produce uniform illuminated images for each illumination source.

According to a second aspect of the present invention there is provided an endoscope having restricted dimensions and comprising at least one image gatherer at least one image distorter and at least one image sensor shaped to fit within said restricted dimensions, and wherein said image distorter is operable to distort an image received from said image gatherer so that the image is sensible at said shaped image sensor substantially with an original image resolution level.

Preferably, the image distorter comprises an image splitter operable to split said image into two part images.

Preferably, the image sensor comprises two sensor parts, each separately arranged along longitudinal walls of said endoscope.

Preferably, the two parts are arranged in successive lengths along opposite longitudinal walls of said endoscope.

Preferably, the distorter is an astigmatic image distorter.

Preferably, the astigmatic image distorter is an image rectangulator and said image sensor comprises sensing pixels rearranged to complement rectangulation of said image by said image rectangulator.

Preferably, the image distorter comprises at least one lens.

Preferably, the image distorter comprises at least one image-distorting mirror.

Preferably, the image distorter comprises optical fibers to guide image light substantially from said lens to said image sensor.

Preferably, the image distorter comprises a second lens.

Preferably, the image distorter comprises at least a second image-distorting mirror.

Preferably, the image distorter comprises at least one flat optical plate.

A preferred embodiment comprises at least one light source for illuminating an object, said light source being controllable to flash at predetermined times.

A preferred embodiment comprises a second light source, said first and said second light sources each separately controllable to flash.

Preferably, the first light source is a white light source and said second light source is an IR source.

In a preferred embodiment, one light source being a right side light source for illuminating an object from a first side and the other light source being a left side light source for illuminating said object from a second side.

In a preferred embodiment, one light source comprising light of a first spectral response and the other light source comprising light of a second spectral response.

A preferred embodiment further comprises color filters associated with said light gatherer to separate light from said image into right and left images to be fed to respective right and left distance measurers to obtain right and left distance measurements for construction of a three-dimensional image.

In a preferred embodiment, said light sources are configured to flash alternately or simultaneously.

A preferred embodiment further comprises a relative brightness measurer for obtaining relative brightnesses of points of said object using respective right and left illumination sources, thereby to deduce 3 dimensional distance information of said object for use in construction of a 3 dimensional image thereof.

A preferred embodiment further comprises a second image gatherer and a second image sensor.

Preferably, the first and said second image sensors are arranged back to back longitudinally within said endoscope.

Preferably, the first and said second image sensors are arranged successively longitudinally along said endoscope.

Preferably, the first and said second image sensors are arranged along a longitudinal wall of said endoscope.

A preferred embodiment comprises a brightness averager operable to identify brightness differentials due to variations in distances from said endoscope of objects being illuminated, and substantially to cancel said brightness differentials.

A preferred embodiment further comprises at least one illumination source for illuminating an object with controllable width light pulses and wherein said brightness averager is operable to cancel said brightness differentials by controlling said widths.

A preferred embodiment has at least two controllable illumination sources, one illumination source for emitting visible light to produce a visible spectrum image and one illumination source for emitting invisible (i.e. IR or UV) light to produce a corresponding spectral response image, said endoscope being controllable to produce desired ratios of visible and invisible images.

According to a third aspect of the present invention there is provided an endoscope system comprising an endoscope and a controller, said endoscope comprising:
at least one image gatherer,
at least one image distorter and
at least one image sensor shaped to fit within restricted dimensions of said endoscope, said image distorter being operable to distort an image received from said image gatherer so that the image is sensible at said shaped image sensor with retention of image resolution,
said controller comprising a dedicated image processor for processing image output of said endoscope.

Preferably, the dedicated image processor is a motion video processor operable to produce motion video from said image output.

Preferably, the dedicated image processor comprises a 3D modeler for generating a 3D model from said image output.

Preferably, the said dedicated image processor further comprises a 3D imager operable to generate a stereoscopic display from said 3D model.

A preferred embodiment comprises an image recorder for recording imaging.

A preferred embodiment comprises a control and display communication link for remote control and remote viewing of said system.

Preferably, the image distorter comprises an image splitter operable to split said image into two part images.

Preferably, the image sensor comprises two sensor parts, each separately arranged along longitudinal walls of said endoscope.

Preferably, the two parts are arranged in successive lengths along opposite longitudinal walls of said endoscope.

Preferably, the distorter is an astigmatic image distorter.

Preferably, the astigmatic image distorter is an image rectangulator and said image sensor comprises sensing pixels rearranged to complement rectangulation of said image by said image rectangulator.

Preferably, the image distorter comprises at least one lens.

Preferably, the image distorter comprises at least one image-distorting mirror.

Preferably, the image distorter comprises optical fibers to guide image light substantially from said lens to said image sensor.

Preferably, the image distorter comprises a second lens.

Preferably, the image distorter comprises at least a second image-distorting mirror.

Preferably, the image distorter comprises at least one flat optical plate.

A preferred embodiment further comprises at least one light source for illuminating an object.

A preferred embodiment comprises a second light source, said first and said second light sources each separately controllable to flash.

Preferably, the first light source is a white light source and said second light source is an invisible source.

In a preferred embodiment, one light source is a right side light source for illuminating an object from a first side and the other light source is a left side light source for illuminating said object from a second side.

In a preferred embodiment, one light source comprises light of a first spectral response and the other light source comprises light of a second spectral response.

A preferred embodiment comprises color filters associated with said light gatherer to separate light from said image into right and left images to be fed to respective right and left distance measurers to obtain right and left distance measurements for construction of a three-dimensional image.

Preferably, the light sources are configured to flash alternately or simultaneously.

A preferred embodiment further comprises a relative brightness measurer for obtaining relative brightnesses of points of said object using respective right and left illumination sources, thereby to deduce 3 dimensional distance information of said object for use in construction of a 3 dimensional image thereof.

A preferred embodiment further comprises a second image gatherer and a second image sensor.

Preferably, the first and said second image sensors are arranged back to back longitudinally within said endoscope.

Preferably, the first and said second image sensors are arranged successively longitudinally along said endoscope.

Preferably, the first and said second image sensors are arranged along a longitudinal wall of said endoscope.

A preferred embodiment comprises a brightness averager operable to identify brightness differentials due to variations in distances from said endoscope of objects being illuminated, and substantially to reduce said brightness differentials.

According to a fifth embodiment of the present invention there is provided an endoscope for internally producing an image of a field of view, said image occupying an area larger than a cross-sectional area of said endoscope, the endoscope comprising:
an image distorter for distorting light received from said field of view into a compact shape, and
an image sensor arranged in said compact shape to receive said distorted light to form an image thereon.

A preferred embodiment comprises longitudinal walls, wherein said image sensor is arranged along said longitudinal walls, the endoscope further comprising a light diverter for diverting said light towards said image sensor.

Preferably, the image sensor comprises two parts, said distorter comprises an image splitter for splitting said image into two parts, and said light diverter is arranged to send light of each image part to a respective part of said image sensor.

Preferably, the sensor parts are aligned on facing lengths of internal sides of said longitudinal walls of said endoscope.

Preferably, the sensor parts are aligned successively longitudinally along an internal side of one of said walls of said endoscope.

A preferred embodiment of the image distorter comprises an astigmatic lens shaped to distort a square image into a rectangular shape of substantially equivalent area.

A preferred embodiment further comprises a contrast equalizer for compensating for high contrasts differences due to differential distances of objects in said field of view.

A preferred embodiment comprises two illumination sources for illuminating said field of view.

In a preferred embodiment, the illumination sources are controllable to illuminate alternately, and said image sensor is controllable to gather images in synchronization with said illumination sources thereby to obtain independently illuminated images.

In a preferred embodiment, each illumination source is of a different predetermined spectral response.

A preferred embodiment of said image sensor comprises pixels, each pixel being responsive to one of said predetermined spectral responses.

A preferred embodiment of the image sensor comprises a plurality of pixels responsive to white light.

In a preferred embodiment, said image sensor comprises a plurality of pixels responsive to different wavelengths of light.

In a preferred embodiment, the wavelengths used comprise at least three of red light, green light, blue light and infra-red light.

In a preferred embodiment, a second image sensor forms a second image from light obtained from said field of view.

In a preferred embodiment, said second image sensor is placed in back to back relationship with said first image sensor over a longitudinal axis of said endoscope.

In a preferred embodiment, the second image sensor is placed in end to end relationship with said first image sensor along a longitudinal wall of said endoscope.

In a preferred embodiment, the second image sensor is placed across from said first image sensor on facing internal longitudinal walls of said endoscope.

According to a sixth embodiment of the present invention there is provided a compact endoscope for producing 3D images of a field of view, comprising a first image sensor for receiving a view of said field through a first optical path and a second image sensor for receiving a view of said field through a second optical path, and wherein said first and said second image sensors are placed back to back along a longitudinal axis of said endoscope.

According to a seventh embodiment of the present invention there is provided a compact endoscope for producing 3D images of a field of view, comprising a first image sensor for receiving a view of said field through a first optical path and a second image sensor for receiving a view of said field through a second optical path, and wherein said first and said second image sensors are placed end to end along a longitudinal wall of said endoscope.

According to an eighth embodiment of the present invention there is provided a compact endoscope for producing 3D images of a field of view, comprising two illumination sources for illuminating said field of view, an image sensor for receiving a view of said field illuminated via each of said illumination sources, and a view differentiator for differentiating between each view.

Preferably, the differentiator is a sequential control for providing sequential operation of said illumination sources.

Preferably, the illumination sources are each operable to produce illumination at respectively different spectral responses and said differentiator comprises a series of filters at said image sensor for differentially sensing light at said respectively different spectral responses.

Preferably, the image distorter comprises a plurality of optical fibers for guiding parts of a received image to said image sensor according to said distortion pattern.

According to a ninth embodiment of the present invention there is provided a method of manufacturing a compact endoscope, comprising:

providing an illumination source,
providing an image distorter,
providing an image ray diverter,
providing an image sensor whose shape has been altered to correspond to a distortion built into said image distorter, said distortion being selected to reduce at least one dimension of said image sensor to less than that of an undistorted version being sensed, assembling said image distorter, said image ray diverter and said image sensor to form an optical path within an endoscope According to a tenth embodiment of the present invention there is provided a method of obtaining an endoscopic image comprising:

illuminating a field of view,
distorting light reflected from said field of view such as to form a distorted image of said field of view having at least one dimension reduced in comparison to an equivalent dimension of said undistorted image, and sensing said light within said endoscope using at least one image sensor correspondingly distorted.

BRIEF DESCRIPTION OF THE DRAWINGS

For a better understanding of the invention and to show how the same may be carried into effect, reference will now be made, purely by way of example, to the accompanying drawings, in which.

DESCRIPTION OF THE PREFERRED EMBODIMENTS

The present embodiments provide a diagnostic and operative system for minimally invasive diagnosis and surgery procedures, and other medical and non-medical viewing applications, in particular in which access conditions dictate the use of small-dimension viewing devices.

Figure 1:
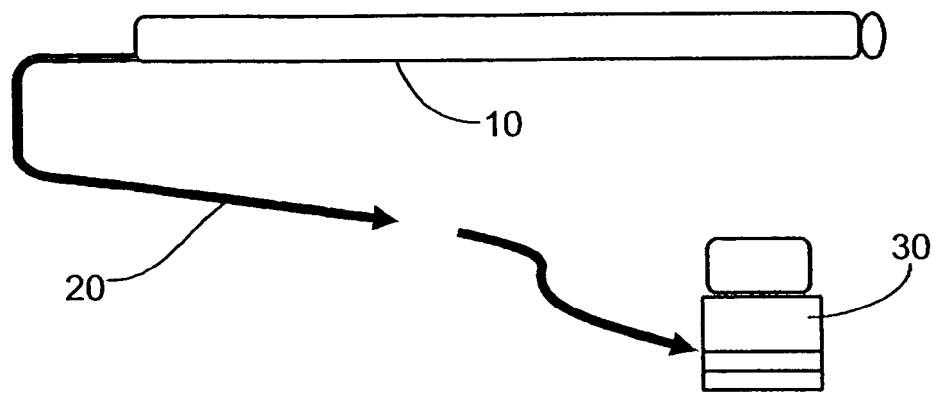
FIG. 1 is a simplified block diagram of an endoscope system to which embodiments of the present invention may be applied.

Reference is now made to FIG. 1, which is a basic block diagram of a basic configuration of an endoscope according to a first embodiment of the present invention. The figure snows a basic configuration of the endoscopic system including interconnections. The configuration comprises a miniature endoscopic front-end 10, hereinafter simply referred to as an endoscope, attached by a wire connection 20 to a processing device 30, typically a PC, the PC having appropriate software for carrying out image processing of the output of the endoscope. The skilled person will appreciate that the wire connection 20 may be an optical connection or may instead use RF or a like means of wireless communication. The miniature endoscopic front-end 10 may be designed for connection to any standard PC input (the USB input for example).

The software included with processing device 30 processes the output of the miniature endoscopic front-end 10. The software may typically control transfer of the images to the monitor of the PC 30 and their display thereon including steps of 3D modeling based on stereoscopic information as will be described below, and may control internal features of the endoscopic front end 10 including light intensity, and automatic gain control (AGC), again as will be described below.

Figure 2:
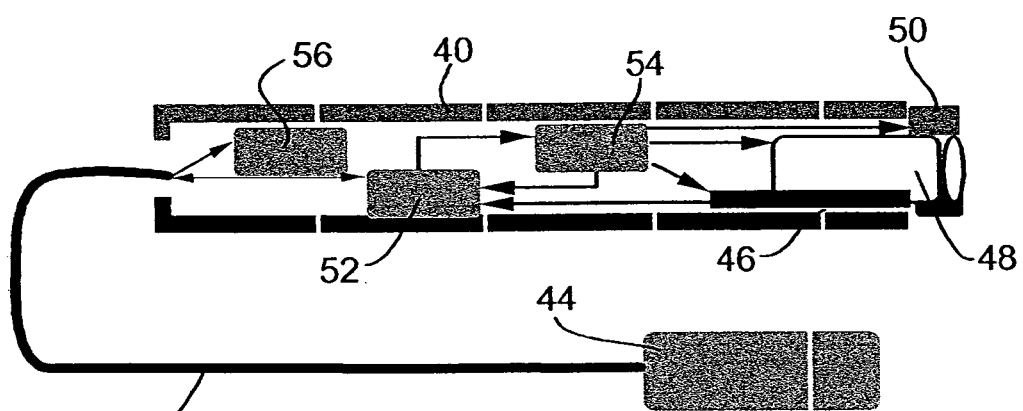
FIG. 2 is a simplified block diagram of an endoscope system according to a first embodiment of the present invention.

Reference is now made to FIG. 2, which is an internal block diagram of an endoscope according to a preferred embodiment of the present invention. A miniature endoscope 40 is connected by a wire 42 to an adapter 44. The endoscope 40 comprises an image sensor 46 which may typically comprise a CMOS or CCD or like sensing technology, an optical assembly 48, a light or illumination source 50, communication interface 52 and controller 54. The wired unit of FIG. 2 preferably includes a voltage regulator 56.

As will be explained in more detail below, the image sensor 46 is aligned along the length of a longitudinal side-wall (that is to say substantially in parallel with the wall and at least not perpendicular thereto) of the endoscope 40. Such an alignment enables the radial dimension of the endoscope to be reduced beyond the diagonal of the image sensor 46. Preferably the sensor is arranged in two parts, as will be explained below.

Figure 3:
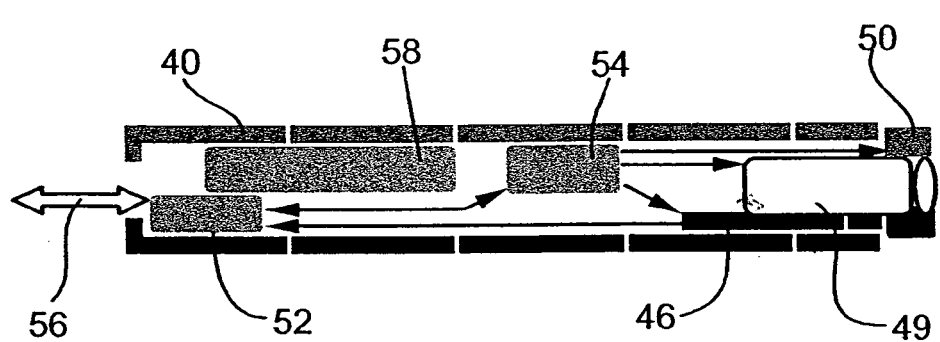
FIG. 3 is a simplified block diagram of a wireless modification of the endoscope of FIG. 2.

Reference is now made to FIG. 3, which is an internal block diagram of a wireless equivalent of the embodiment of FIG. 2. Parts that are identical to those shown above are given the same reference numerals and are not referred to again except as necessary for an understanding of the present embodiment. In the embodiment of FIG. 3, the wire 42 is replaced by a wireless link 56 such as an IR or RF link with appropriate sensor, and a battery pack 58.

Figure 4:
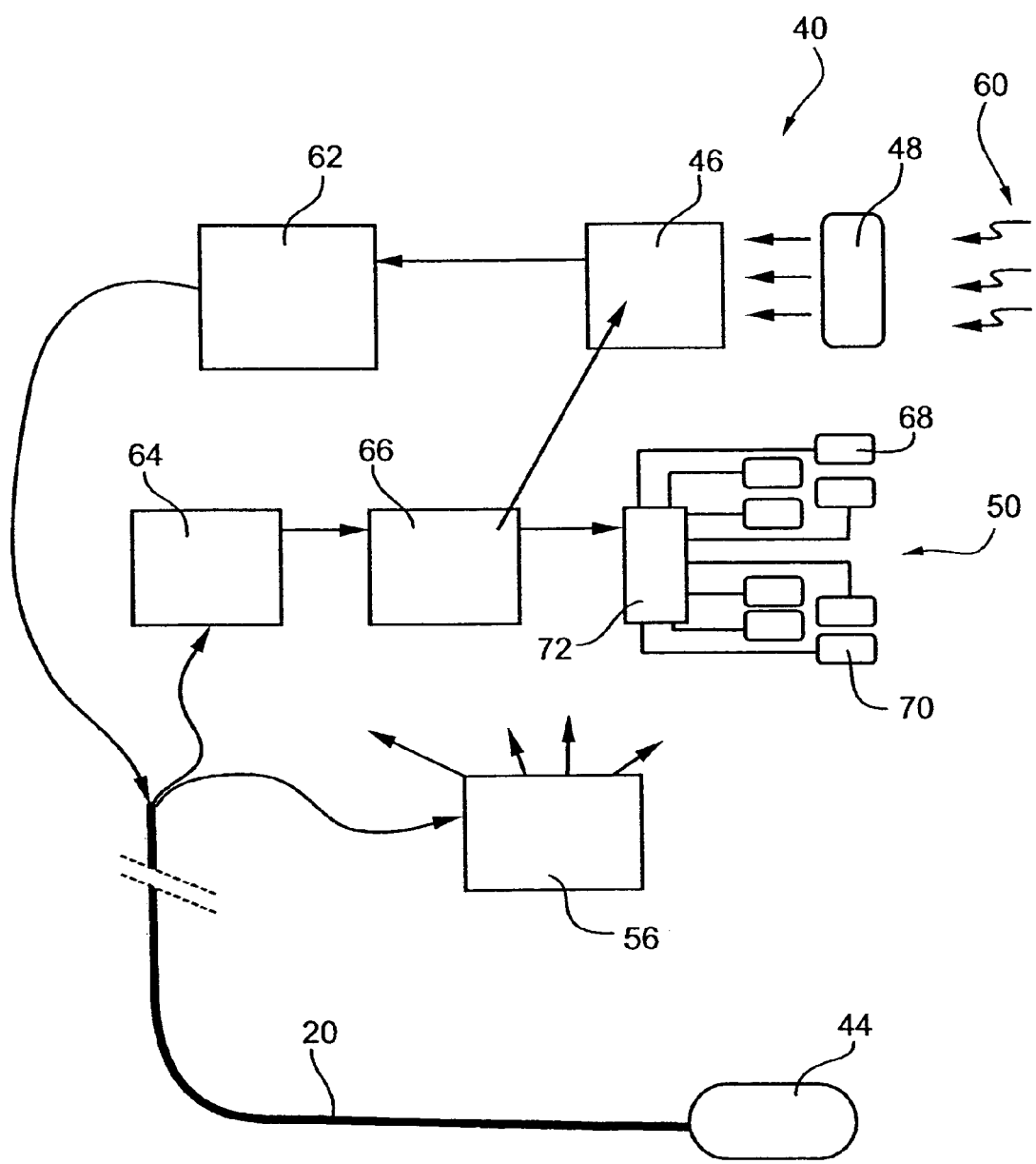
FIG. 4 is a simplified schematic block diagram of an endoscope according to a preferred embodiment of the present invention.

Reference is now made to FIG. 4, which is an schematic block diagram of the miniature endoscope according to a preferred embodiment of the present invention. Parts that are identical to those shown above are given the same reference numerals and are not referred to again except as necessary for an understanding of the present embodiment. Optical assembly 48 receives light, indicated by arrows 60, from an object being viewed. The light is processed by optical assembly 48, as will be explained below, to reach image sensor 46 were it is converted from photons into electrical signals. The electrical signals are digitized and passed to a transmitting device 62, for example an LVDS transmitter, which drives the data through communication link 20 and adapter 44 to the processing device 30.

Operating power for the endoscope 40 is preferably provided, through adapter 44, to the voltage regulator 56. Control of the front-end is preferably carried out by the processor device 30 as discussed above. Control data from the processing device 30 is preferably received at the endoscope 40 by a receiving device 64, which may typically be an LVDS receiver. Hard wired logic 66 preferably serves as an interface to convert the incoming control data into signals for controlling both the sensor 46 and the light source 50.

The light source 50 preferably comprises one or more light transmitting devices such as LEDs, typically a left light source 68 and right light source 70. The left and right light sources may be controllable through a driver 72. The functions of each of the above components are described in greater detail below. As the skilled person will be aware, use of CMOS and similar technologies for the sensors permit the sensor 46, the transmitting device 62, the receiving device 64, the hard wired logic 66, the driver 72 and the voltage regulator 56 to be integrated into a single semiconductor Integrated Circuit and such integration is particularly advantageous in achieving a compact design of endoscope.

Considering the light source 50 in greater detail, it preferably comprises an integrated array of several white light sources (LEDs for example) with energy emission in the visible light range mixed, optionally, with IR light sources (LEDs) for purposes that will be explained below. In fact, any combination of spectral responses may be used, particularly preferred combinations including red+IR and green+blue. An integrated array of light sources allows control of each light source individually facilitating the following features:

The System is able to turn on the white light source and the IR Light source in sequence to generate an IR image every N (user determined) standard white images, for detection by a sensor configuration to be described below with respect to FIG. 12.

The objects being imaged are generally located at a range of different distances or field depths from the light source and are consequently unevenly illuminated. The more distant areas in the field are dark and are almost invisible while the nearer areas are bright and can become saturated. In order to compensate for the uneven illumination intensity over the field, the system preferably exerts control over the intensity of each light source individually, thereby to compensate for reflected intensity of the objects. An example of an algorithm for control of the illumination array is given as follows:

Given N individual light sources in the illumination array in the camera head, an initialization process is carried out to generate a reference image, preferably a homogeneous white object, to be stored for each light source. The stored reference images (matrices) are identified hereinbelow by RIi where i=1, 2, ... N Following initialization, imaging is carried out and the input image of the field (indicated by matrix II) is divided into M areas such that: M>N. The image areas are identified hereinbelow by Sj j=1, 2, ... M Following the above imaging stage, an inner product matrix is calculated such that element Tij of the inner product matrix reflects the inner product resulting from taking the II matrix and performing matrix multiplication with the RIi matrix, in the area Sj and summing the elements of the result metrics.

The resulting inner product matrix is given by T where:

$$T = \begin{vmatrix} t11 & t12 & \ldots & t1M \\ t21 & \ldots & \ldots & t2M \\ tN1 & \ldots & \ldots & tNM \end{vmatrix} N \text{ and}$$

$$Tij = 1/Sj \sum_{P=1}^{Sj} Pij(xp, yp) \cdot Rj(xp, yp)$$

wherein

Pij—the intensity of the pixel located in (xp, yp) resulting from light source i in area j Rj—the intensity of the pixel located in (xp, yp) resulting from the input image in area j Sj—the total pixels in area j xp, yp—the pixels coordinates in area j Next, a vector v is determined that satisfies the following:

Tv−k→Min, where v—the vector of intensities of each source, and k—the vector of the desired common intensity, and the solution to this requirement is given by $$\underline{v} = (T^T \cdot T)^{-1} \cdot T^T \cdot \underline{k}$$

The central control unit preferably uses the above algorithm to post-process the data to reconstruct a natural look of the image, thereby to compensate for brightness non-uniformities.

In the case of using LEDs as the light source, their fast response time makes it possible to operate them in a "controllable-flash" mode, replacing the need for variable integration time (or AGC).

Referring now to the image sensor 46, as observed above in respect of FIG. 2, in the prior art endoscope the size of the sensor provides a limitation on the transverse diameter of the endoscope. Thus, in the present embodiment, in order to remove the limitation the sensor is placed along the longitudinal wall of the endoscope, again preferably substantially parallel to the wall but at least not perpendicular thereto. The use of the longitudinal wall not only gives greater freedom to reduce the transverse diameter of the endoscope but also gives the freedom to increase the length of the sensor, thus increasing image resolution in the horizontal sense.

As will be explained below, there are two specific embodiments of the realigned sensor, each one associated with a respective design of the optical assembly as will be described in detail below.

In addition to the above-mentioned geometrical realignment, the sensor may be supplied with color filters to allow acquisition of IR images for diagnostic purposes or 3D imaging, again as will be described in detail below.

Referring now to the geometric design of the sensor, as will be appreciated, the sensor comprises a field of pixels arranged in an array over an image-gathering field. The first specific embodiment comprises a rearrangement of the pixels in the sensor. Given that for the purposes of example, the sensor width may be divided into say two parts, then the two parts may be placed end to end lengthwise. Thus, for example, a 512×512 pixels' sensor with pixel dimensions of 10×10 micron, may be divided into two sections of width 256 pixels each to be placed end to end to give a sensor of 256×1024 pixels and having an overall imaging area of 2.56 mm×10.24 mm. The longer dimension is preferably placed along the lengthwise dimension of the endoscope, thus permitting reduced diameter of the endoscope with no corresponding reduction in the precision level of the image.

The second specific embodiment likewise relates to a geometrical rearrangement of the pixels. The prior art image sensor has a round or square overall sensor or pixilated area, however, if the same number of pixels are arranged as a rectangle having the same area as the original sensor but with the height and width freely chosen then the width may be selected to be smaller than the width of the equivalent prior art sensor. More particularly, for an exemplary 512×512 pixels' sensor with pixel dimensions of 10×10 micron the standard prior art sensor (which will have a width of 5.12 mm) may be replaced by a rectangular sensor having the same overall sensing area as in the previous specific embodiment, but with specific width height dimensions of 2.56 mm×10.24 mm, thus becoming easier to fit in the endoscope.

Figure 5:
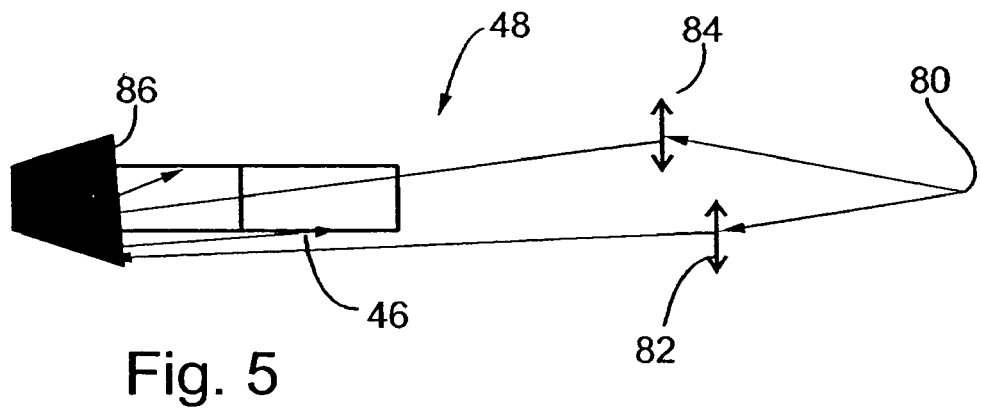
FIG. 5 is a simplified ray diagram showing optical paths within an endoscope according to a preferred embodiment of the present invention.

Reference is now made to FIG. 5, which is a ray diagram showing a simplified view from above of optical paths within the endoscope. As will be appreciated, in order for the image sensors of the specific embodiments referred to above to produce images which can be recreated in an undistorted fashion, each sensor is preferably associated with an optical assembly which is able to redirect image parts in accordance with the rearrangements of the pixels.

Figure 6:
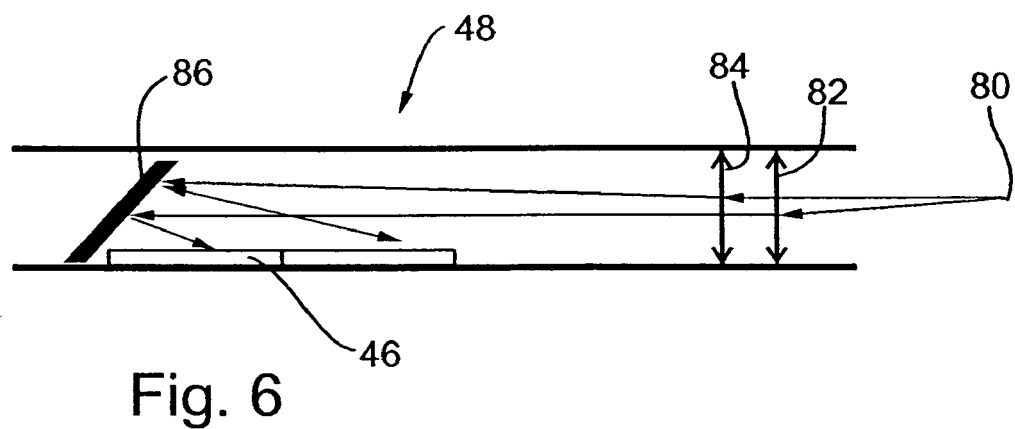
FIG. 6 is a ray diagram view from a different angle of the embodiment of FIG. 5.

FIG. 5 shows a version of optical assembly 48 designed for the first of the two specific embodiments of the image sensor, namely that involving the widthwise transfer of pixels. A side view of the same optical assembly is shown in FIG. 6. FIG. 5 shows a point source object 80, from which light reaches two lenses 82 and 84. The two lenses are selected and arranged to divide the light into two parts, which parts reach a front-surface-mirror 86. The front surface mirror sends each part of the image to a different part of the sensor 46, and recovery of the image is possible by appropriate wiring or addressing of the sensor pixels to recover the original image shape.

Figure 7:
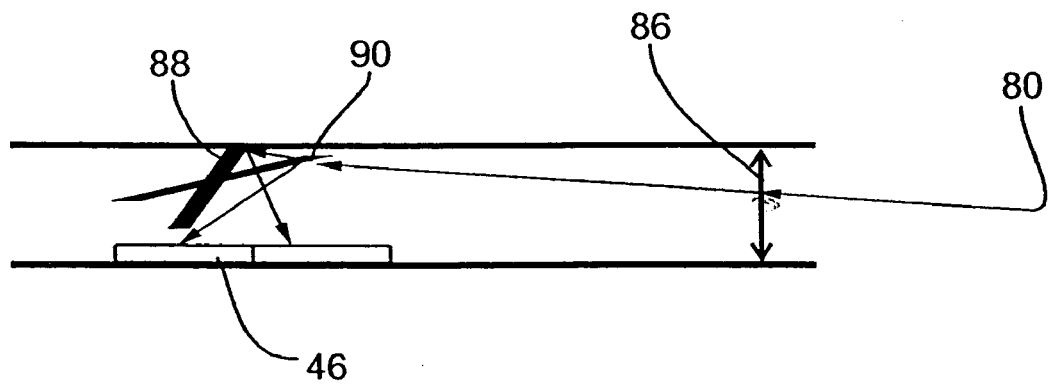
FIG. 7 is a ray diagram showing an alternative construction of an optical assembly according to a preferred embodiment of the present invention.

Reference is now made to FIG. 7 which is a ray diagram showing an alternative version of optical assembly 48, again designed for the first specific embodiment of the image sensor. A single lens 86 is positioned in conjunction with two front-surface-mirrors 88 and 90 to deflect light from the object 80 to the mirrors. Each of the two front surface mirrors respectively transfers half of the image to the upper or lower part of the sensor 46.

Figure 8:
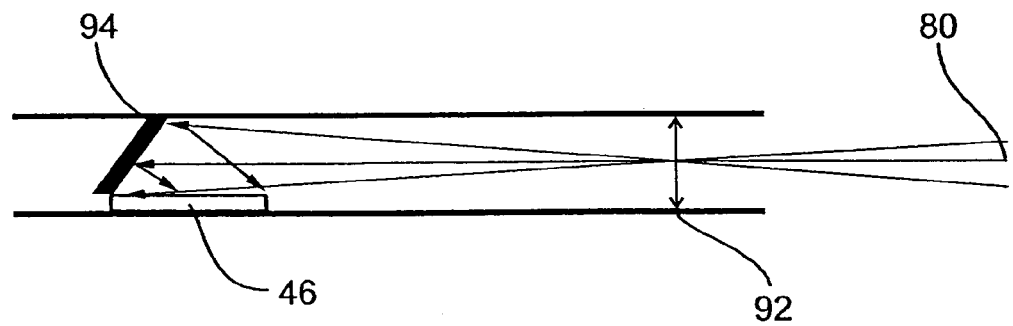
FIG. 8 is a ray diagram showing a further alternative construction of an optical assembly according to a preferred embodiment of the present invention.

Reference is now made to FIG. 8, which is a ray diagram showing a third embodiment of the optical assembly 48, this time for the second of the specific embodiments of the image sensor 46, namely the embodiment in which the square shape of pixels is reduced to a rectangular shape having smaller width. An asymmetric or astigmatic lens 92 is arranged to focus light onto a front-surface-mirror 94. The light is distorted by the lens 92 to undo the distortion introduced into the image by the rectangular shape of the sensor 46, and then it is reflected by the mirror 94 onto the surface of the sensor 46.

Figure 9:
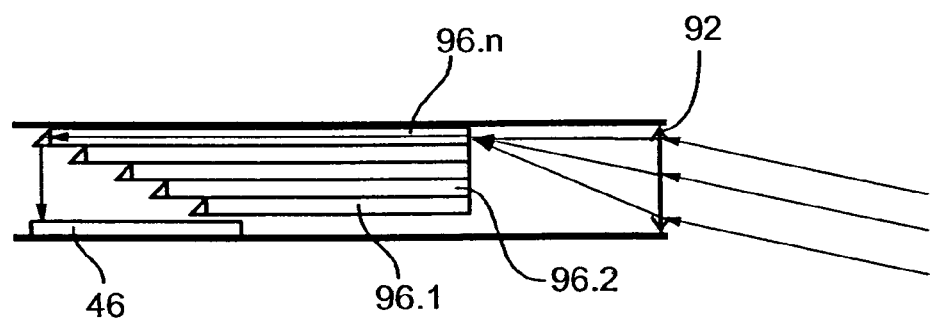
FIG. 9 is a ray diagram showing yet a further alternative construction of the optical assembly according to a preferred embodiment of the present invention.

Reference is now made to FIG. 9, which is a ray diagram taken from the side showing a further embodiment of the optical assembly 48. The embodiment of FIG. 8 necessitates a relatively complicated design of the mirror, and in order to obviate such complexity, additional optical des is shown. As shown in FIG. 9, the same astigmatic lens 92 is placed, not in front of a mirror but rather in front of a series of flat optical plates 96.l. . . 96.n, each comprising a diagonal lateral cross section, the plates each reflecting the light through the respective plate to the surface of sensor 46.

Figure 10:
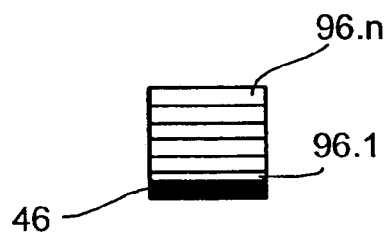
FIG. 10 is a ray diagram taken from the front, of the embodiment of FIG. 9.

Reference is additionally made to FIG. 10, which is a ray diagram, taken from the front, of the series of optical plates 96 of FIG. 9. A comparison between the perspectives of FIG. 9 and FIG. 10 show the layout of the plates with respect to the endoscope.

Figures 11, 12:
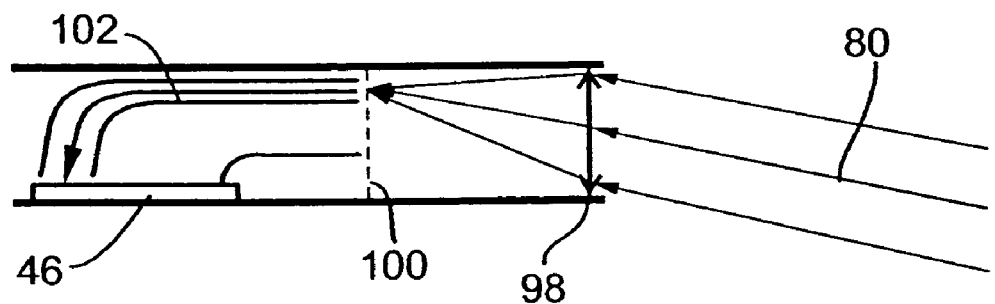
FIG. 11 is a ray diagram showing yet a further alternative construction of an optical assembly according to a preferred embodiment of the present invention.
FIG. 12 is a simplified layout diagram of an image sensor according to an embodiment of the present invention.

Reference is now made to FIG. 11, which is a simplified ray diagram showing a further embodiment of the optical assembly 48. In the embodiment of FIG. 11, a single lens 98 is preferably used to focus light from an object 80 to a plane 100 shown in dotted lines. A series of optical fibers 102 are lined up over the surface of plane 100 to guide light to desired portions of the surface of the image sensor 46. The fibers 102 are able to direct light as desired and thus can be used in combination with any arrangement of the sensor pixels that is desired.

Returning to the construction of the image sensor 46, reference is now made to FIG. 12, which is a layout diagram showing a layout of pixels on a sensory surface of an embodiment of the image sensor 46. In FIG. 12, an array comprising pixels of four types is shown, red r, green g, blue b and infra-red IR. The pixels are evenly spaced and allow acquisition of a colored image when used in conjunction with white light or an IR image when used in conjunction with an IR source.

In many cases, important medical information is contained at IR wavelengths. In order to allow acquisition of IR images, the sensor is preferably designed as described above, and using inter alia pixels IR filters, that is to say color filters that have band passes at IR wavelengths. The sensor is placed in an endoscope in association with either one or both of a source of visible light and a source of infra-red light. Use of the appropriate one of the two light sources permits acquisition of either color frames or IR frames as desired. In one preferred embodiment, IR and color frames are obtained simultaneously by operating color and IR light sources together and allowing each pixel to pick up the waveband it has been designed for. In another preferred embodiment the color and IR light sources are operated separately. Typically one IR frame would be prepared and sent for every several color frames.

Figure 13:
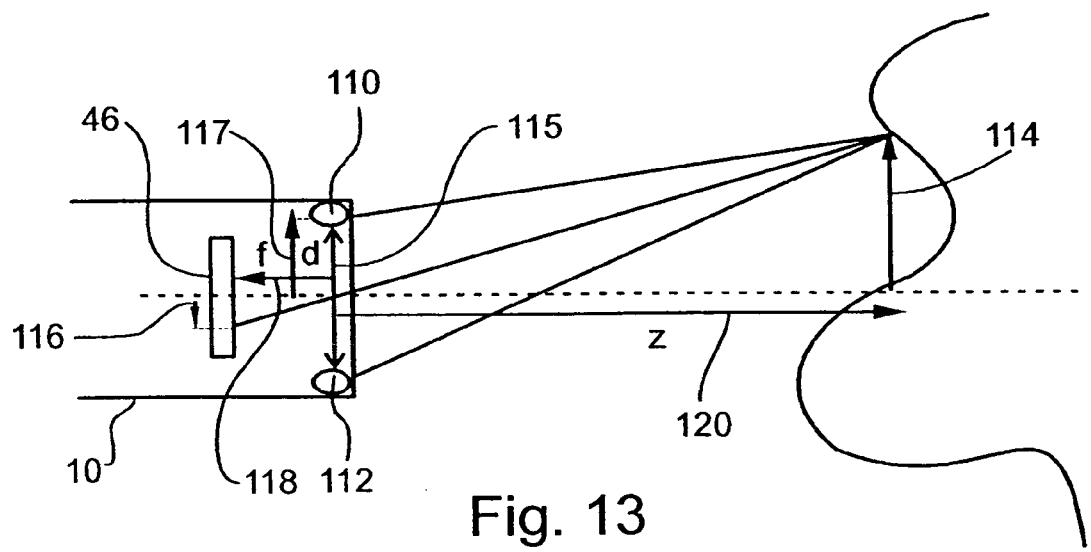
FIG. 13 is a simplified ray diagram showing an endoscope for use in a stereoscopic mode according to a preferred embodiment of the present invention.

Reference is now made to FIG. 13, which is a simplified ray diagram showing how the endoscope may be used in a stereoscopic mode. The stereoscopic mode permits the production of 3D images. As with previous figures the ray diagram indicates rays emanating from a single point, and the skilled person will appreciate how to extrapolate to a full image.

In FIG. 13, an endoscope comprises two separate white light sources 110 and 112 located at opposite sides of a front opening of the endoscope, respectively being a left light source 110 and a right light source 112. The two white light sources are controlled to light in turn in successive short flashes to illuminate an object 114. Light reflected by the object 114 returns to the endoscope where it strikes a lens 115 placed across the front opening and where it is focused on to the plane of sensor 46. The sensor detects the illumination level, which differs between the left and right light beams. The ratio of the illumination levels may be used to calculate the position of the object and thereby to build up a 3D distance database, as will be explained in greater detail below.

As mentioned above, in the stereoscopic mode the left and right light sources are used sequentially. Comparison between left and right illuminated images allows a 3D database to be constructed, enabling stereoscopic display of the scene. In the present embodiment, the comparison between the images is based upon photometry measurements. In FIG. 13, an image 116 of object 114 may be considered as comprising a series of activated x, y, locations on the detection plane of the sensor 46. For each of the x, y locations forming the image 116 on the sensor 46, a ratio between the Right Illuminated Image (RII) and the Left Illuminated Image (LII) may be discerned. The detected ratio may differ over the image as it is a function in each case of the distances of the respective light source to the object 114. The left light source 110 and the right light source 112 have a distance between them which is twice d, d being the length of arrow 117, and the lens has a focal length of 1/f, where f is the length of arrow 118. The distance from the lens 115 to the plane of the object 114 is denoted by Z and is indicated by arrow 120.

The Left Beam Length (LBL) can thus be expressed by:

$$LBL = \sqrt{[Z^2 + (X-d)^2]} + \sqrt{[(Z+1/f)^2 + (X+x)^2]}$$

while the Right Beam Length (RBL) is given by:

$$RBL = \sqrt{[Z^2 + (X+d)^2]} + \sqrt{[(Z+1/f)^2 + (X+x)^2]}$$

where:

$$X = xZf$$

Thus the ratio of the light intensity between the left and right light sources, which is the inverted square of the distance LBL/RBL, may be expressed as:

$$\text{LeftToRightRatio} = (LBL/RBL)^{(-2)}$$

The image 116, obtained as described above may now be stored in terms of a 3D model. The 3D model is preferably displayed as a 3D image by constructing therefrom two stereoscopic images. The conversion may be performed using conversion formulae as follows:

$$yl = yr = -Y/(Z*f)$$

$$xl = (-X - D/2)/(Z*t)$$

$$xr = (-X + D/2)/(Z*f)$$

FIG. 13 thus shows how an image of the object can be stored as a 3D data base. 3D data of the object is obtained as described above and stored as a database.

Figure 14:
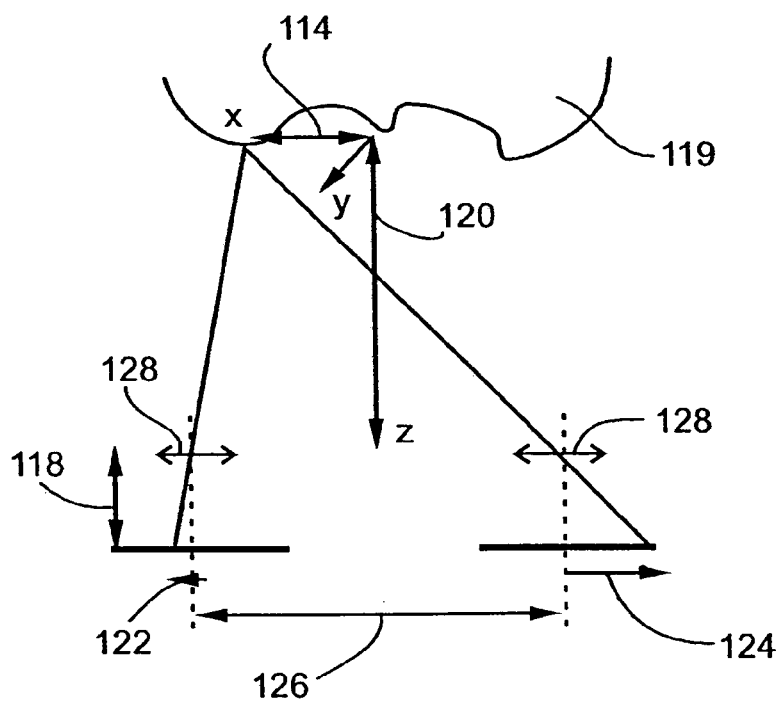
FIG. 14 is a simplified ray diagram showing how a 3D model obtained from the embodiment of FIG. 13 can be used to construct a stereoscopic image of the field of view.

Reference is now made to FIG. 14, which is a further simplified ray diagram showing, by means of rays, how the 3D model or database of FIG. 13 can be used to obtain a 3D effect at the eyes of an observer. In order to display the 3D information using a standard 2D display (monitor) the database is converted into two separate stereoscopic images, and a display device is used to display each one of the stereoscopic images to a different eye. For example the device may be a pair of glasses having a controllable shutter on each on of the eyes.

In FIG. 14, X, Y, 114 and Z 120 represents the three dimensions to be used in the image 119, which corresponds to image 116 as stored in the previous figure, the object being to reproduce the three dimensional character of the image by showing different projections of the image to each of the two eyes of a viewer.

line 122 represents a projected location on the left image.

Line 124 represents the same projected location as it appears on the right image.

1/f 118 is the focal length (the amplification factor).

D 126 is the distance between the lenses 128 (representing the eyes).

A preferred embodiment for producing a 3D model using the endoscope uses different color left and right light sources in place of white light sources. Thus, instead of sequentially illuminating the object from either side, it is possible to illuminate the image simultaneously using both sources and to use appropriate filters to separate the left and right brightness information. For example a left illumination source 110 may be green and right illumination source 112 may be a combination of red+blue. Such a two-color embodiment is advantageous in that it is simple to control and avoids image distortion problems due to the time lag between acquisitions of the two separate images.

In one alternative embodiment, one of the light sources 110, 112 is a visible light source and the second light source is an IR light source. In the case of an IR light source color filters at the sensor preferably include an IR pass filter. The sensor of FIG. 12, with an arrangement of IR, red, green and blue detectors as described above may be used.

Figure 15A:
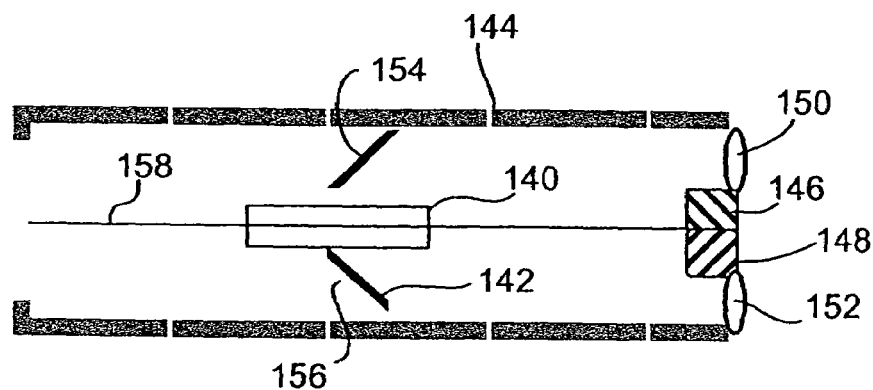
FIG. 15A is a simplified diagram in cross-sectional view showing an arrangement of the image sensors in a stereoscopic endoscope according to a preferred embodiment of the present invention.
Figure 15B:
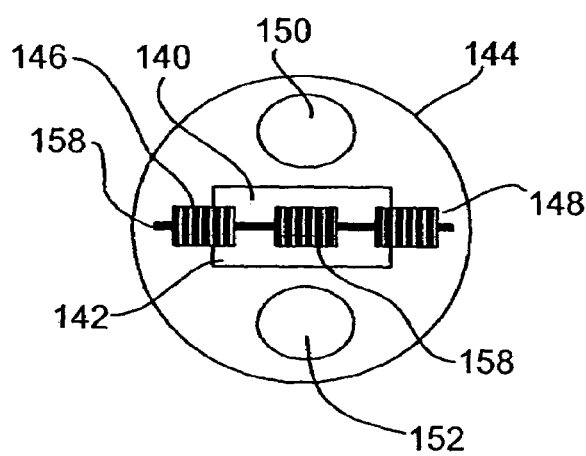
FIG. 15B is a view from one end of the arrangement of FIG. 15A.

Reference is now made to FIGS. 15A and 15B which are simplified schematic diagrams showing an endoscope according to a preferred embodiment of the present invention for obtaining dual sensor stereoscopic imaging, as will be explained below. FIG. 15A is a side sectional view and FIG. 15B is a front view.

In the embodiment of FIG. 15A two image sensors 140 and 142 are situated back to back along a plane of the central axis of an endoscope 144. Each image sensor 140 and 142 is associated with a respective optical assembly comprising a lens 150 and 152 and a mirror 154 and 156. The respective light source 146, 148, illuminates the entire field of view as described above and light is gathered by the lens and directed by the mirror onto the sensor. The sensors are preferably mounted on a single PCB 158.

FIG. 15B is a view from the front of the endoscope of FIG. 15A. It will be noticed that a third optical light source 158 shown. Since the stereoscopic aspect of the image is obtained from the use of two optical image paths, as opposed to the previous embodiments which used different light sources and different object optical paths, there is now freedom to use any number of light sources as desired to produce desired color (or IR) information.

The back-to-back arrangement of the sensors 140 and 142 along the central axis of the endoscope 144 ensures that the endoscope dimensions are minimized both lengthwise and radially.

Figure 16:
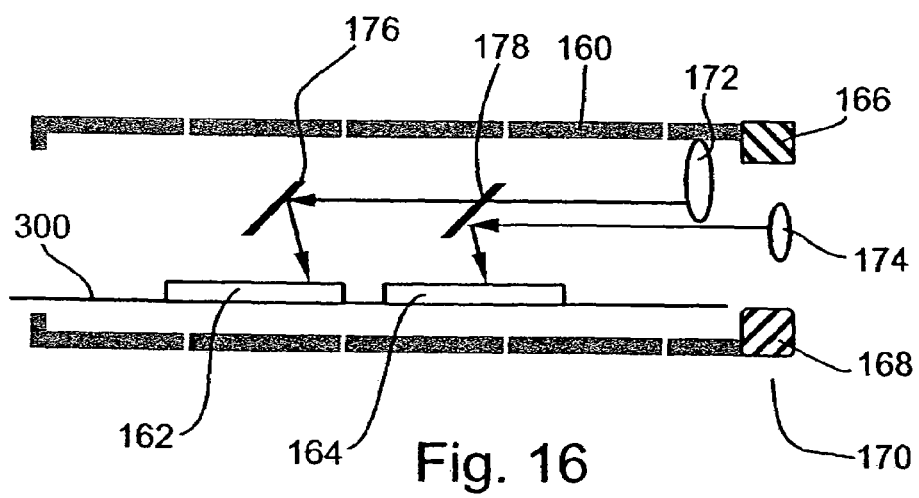
FIG. 16 is a simplified ray diagram showing an alternative arrangement of sensors for obtaining a stereoscopic image of a field of view according to a preferred embodiment of the present invention.

Reference is now made to FIG. 16, which is an alternative embodiment of an endoscope for obtaining dual sensor stereoscopic imaging. An endoscope 160 comprises two image sensors 162 and 164 arranged in a head to tail arrangement along one longitudinal wall of the endoscope, and again, as above, preferably parallel to the wall and at least not perpendicular thereto. Illumination sources 166 and 168 are located at a front end 170 of the endoscope and located at the periphery thereof. Two lenses 172 and 174 direct light received from a field of view onto respective mirrors 176 and 178 each of which is arranged to deflect the light onto one of the sensors. Each image sensor 162 and 164 thus provides a slightly different image of the field of view.

It is emphasized that the dual sensor configuration does not decrease the overall image resolution, because, in accordance with the above configurations, two full-size image sensors may be used.

The two versions of an endoscope for obtaining dual sensor stereoscopic imaging described above can make use of image sensors either with or without color filters. However the sensor of FIG. 12 could be used for one or both of the sensors in either of the embodiments above.

A further preferred embodiment uses a monochrome sensor for one of the two image sensors and a color sensor for the second. Such a combination of one monochrome sensor and one color-filtered sensor in the unit improves the resolution of the overall image and the sensitivity and dynamic range of the endoscope.

The above embodiments have been described in accordance with the general endoscope layout given in FIG. 1. In the following, alternative endoscopic system configurations are described.

Figure 17:
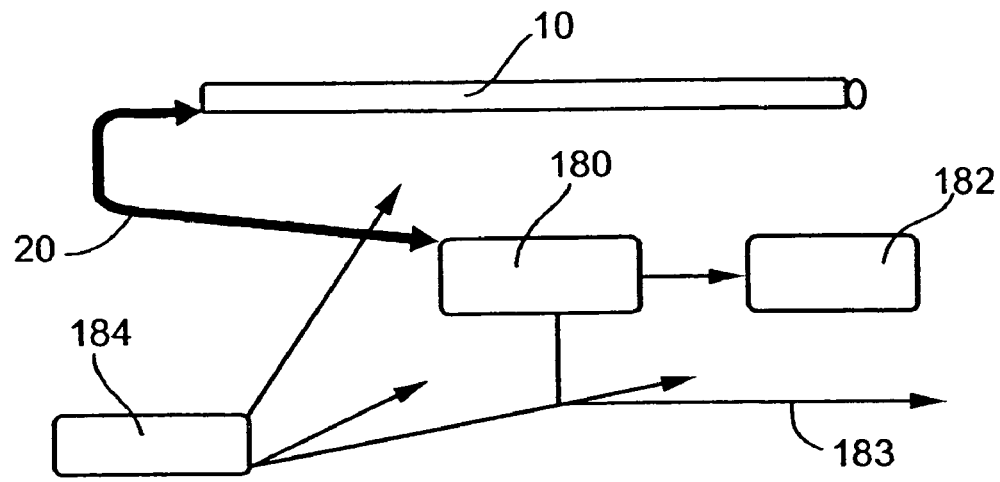
FIG. 17 is a simplified block diagram of a network portable endoscope and associated hardware usable with preferred embodiments of the present invention.

Reference is now made to FIG. 17, which is a simplified block diagram of a network portable endoscope and associated hardware. Parts that are identical to those shown above are given the same reference numerals and are not referred to again except as necessary for an understanding of the present embodiment. An endoscope 10 is connected to a central control unit 180 where dedicated image processing takes place. The control unit 180 allows for full motion video to be produced from the signals emitted by the endoscope. The control unit is connected to a local display device 182. Additionally or alternatively, a remote control and viewing link 183 may be used to allow remote monitoring and control of the endoscope. The endoscope 10 is preferably a portable device and may be powered from a battery pack 184.

Figure 18:
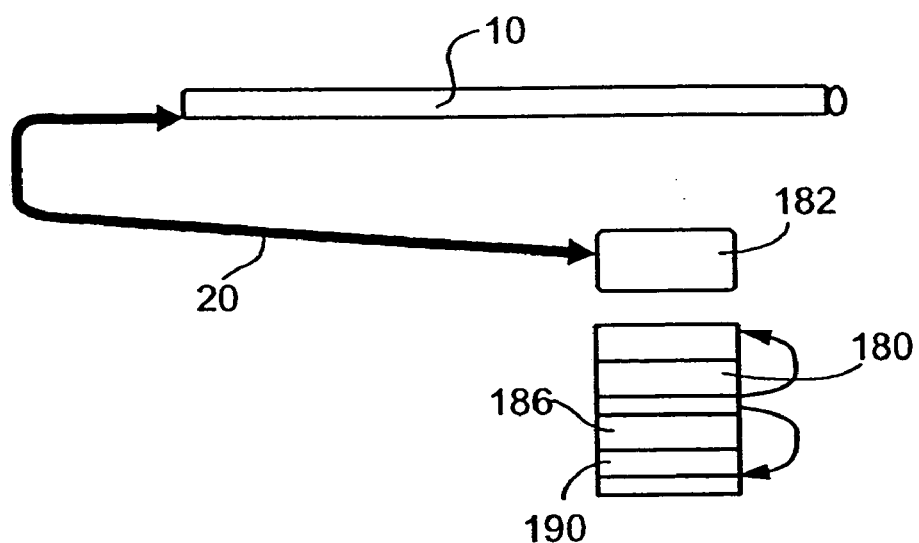
FIG. 18 is a simplified block diagram of an endoscope adapted to perform minimal invasive surgery and usable with the preferred embodiments of the present invention.

Reference is now made to FIG. 18, which is a simplified block diagram of an endoscope adapted to perform minimal invasive surgery (MIS). Parts that are identical to those shown above are given the same reference numerals and are not referred to again except as necessary for an understanding of the present embodiment. The most common use of endoscopic systems is for the performance of MIS procedures by the surgeon in the operating room. The use of a reduced size endoscope according to the above embodiments enables new procedures to be performed in which minimal dimensions of the operating equipment is important. In FIG. 18, the endoscope 10 is connected to a rack 190. The rack contains accomodation for a full range of equipment that may be required in the course of use of the endoscope in the operating room, for example a central control unit 180, a high quality monitor 182, an insufflator 186 etc.

The configuration of FIG. 18, by virtue of the dedicated image processing provided with the control unit 180, gives full motion video without requiring fiber-optic and camera head cables.

Figure 19:
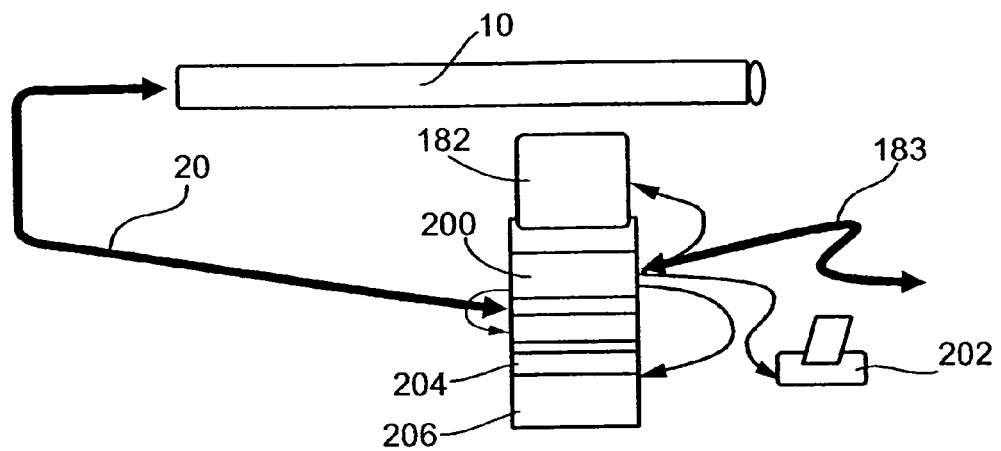
FIG. 19 is a simplified block diagram of an enhanced endoscope system for use in research.

Reference is now made to FIG. 19, which is a simplified block diagram showing an enhanced version of the endoscope for use in research. Parts that are identical to those shown above are given the same reference numerals and are not referred to again except as necessary for an understanding of the present embodiment. The system comprises a miniature endoscopic front-end 10 connected to a highly integrated PC based central control unit 200 via communication link 20.

The central control unit uses dedicated image processing and thus enables full motion video, displayable locally on display device 182 or remotely via control and display link 183. An optional printer 202 is provided to print documents and images, including images taken via the endoscope, of the pathologies or stages of the procedure. The system preferably includes a VCR 204 for recording video produced by the endoscope and a digital storage device 206 allowing archiving of the whole video. As mentioned above, the system can also be connected via remote control and viewing link 183, to a remote site for teaching or for using medical help and guidance. In some hospitals and operating rooms, in addition to regular operating procedures, research is carried out. Research procedures generally require additional documentation and communication functions. In order to support those requirements a PC based system with high documentation and communication capabilities is provided by the enhanced control unit 200. In addition to the external devices, an image enhancement software package is used, allowing the generation of high quality hard copies of images.

Figure 20:
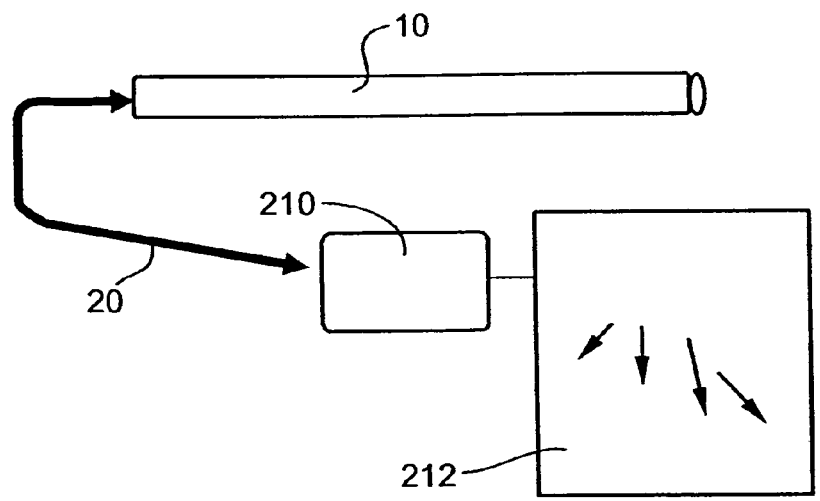
FIG. 20 is a simplified block diagram of a configuration of an endoscope system for obtaining stereoscopic images, and usable with the preferred embodiments of the present invention.

Reference is now made to FIG. 20, which is a simplified block diagram showing a configuration of endoscope for obtaining stereoscopic (3D) images. Parts that are identical to those shown above are given the same reference numerals and are not referred to again except as necessary for an understanding of the present embodiment. The miniature endoscope 10 is connected via a communication link 20 as before to a 3D central control unit 210, which is the same as the previous control unit 200 except that it has the additional capability to construct a 3D model from image information provided by the endoscope. The 3D model can then be projected to form a 3D image on a 3D stereoscopic display system 212. The configuration of FIG. 20 may be combined with features taken from any of the embodiments referred to above.

Recently, new operating procedures requiring stereoscopic (3D) display have been developed. In particular such new applications involved minimally invasive heart and brain procedures. The 3D imaging embodiments referred to above, which may be grouped into multiple light source based imaging and dual optical path imaging, can give the necessary information to construct a 3D model of the scene and to generate stereoscopic images therefrom.

Figure 21:
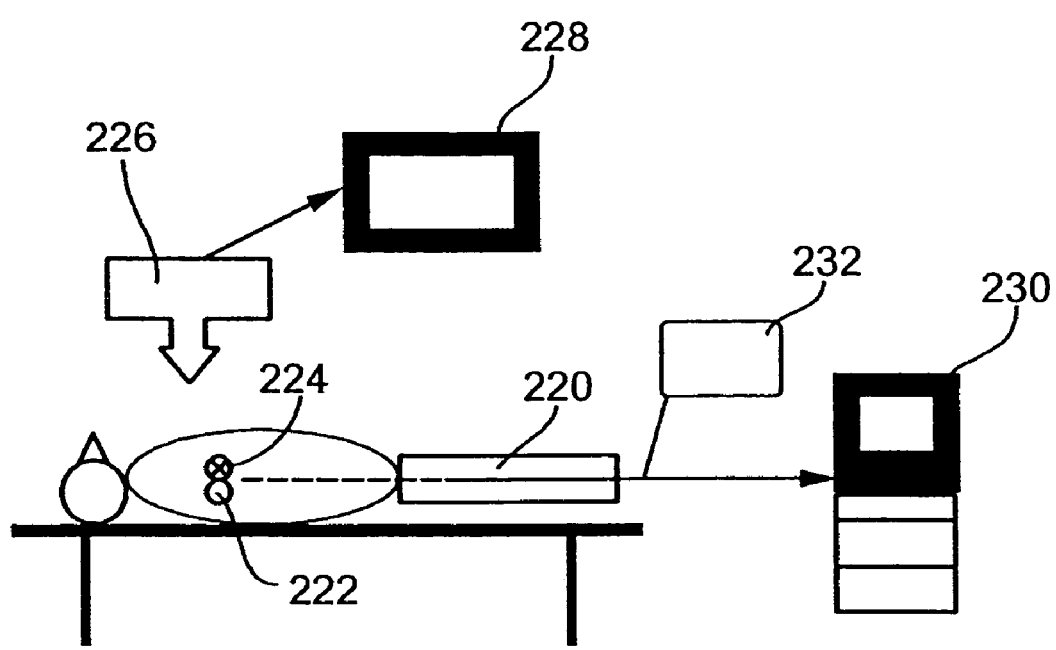
FIG. 21 is a simplified block diagram of a system for use in intravascular procedures.

Reference is now made to FIG. 21, which is a simplified block diagram showing a variation of an endoscope system for use in intra-vascular procedures. Parts that are identical to those shown above are given the same reference numerals and are not referred to again except as necessary for an understanding of the present embodiment. The system includes a long, flexible, thin and preferably disposable catheter 220, a balloon/Stent 222, an endoscope imaging head 224, an X-ray tube 226, X-ray imaging system 228, a video display system 230 and an injection unit 232.

Intra Vascular procedures are widely used in the medical field. Among various intra-vascular procedures, cardiac catheterization is a very common diagnostic test performed thousands of times a day. During the procedure, catheter 220 is inserted into an artery at the groin or arm. The catheter is directed retrogradely to the heart and to the origin of the coronary arteries, which supply blood to the heart muscle. A contrast substance ("dye") is injected through the catheter. The use of an x-ray tube, and an endoscope in conjunction with the dye enables a view of the heart chambers and coronary arteries to be obtained. The resulting images may be recorded using an x-ray camera and/or the endoscope systems as described above. If an obstruction is detected in one or more of the coronary arteries, the obstruction may be removed and the artery reopened using techniques such as inserting the balloon and inflating it (PTCA) or inserting a stent, as known to the person skilled in the art.

In intra-vascular operation generally, a few methods may be used to acquire intra-vascular images in the presence of blood. One method is based on the fact that certain near IR wavelengths allow viewing through blood. The method thus involves the use of an IR illumination source and a sensor with IR filters as described above. Another method uses controlled injection of a transparent physiological liquid into the blood vessel in order to dilute the blood prior to the imaging. Yet another method uses a conical dome, a balloon or any other rigid or flexible and inflatable transparent structure in order to improve visibility by "pushing" the blood to the walls of the vessels, thus enlarging the part of the optical path that does not include blood. Another way of improving visibility is by using a post-processing algorithm after the acquiring of the image has been done. The post-processing algorithm is based on the extraction of parameters from the received image and the use of those parameters in an inverse operation to improve the image.

There is thus provided an endoscope of reduced dimensions which is able to provide 2D and 3D images, and which is usable in a range of minimally invasive surgical procedures.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

The invention claimed is:

1. An endoscope that gathers light, the endoscope having a longitudinal dimension along which the endoscope has a tubular cross-section with an internal diameter, the endoscope comprising: at least one image distorter, and at least one image sensor disposed within the endoscope at a location characterized by the cross-section, said at least one image sensor having a rectangular sensing field, the rectangular sensing field having an image resolution level and having a maximum diagonal dimension that is greater than the endoscope's internal diameter, and said at least one image distorter distorting the gathered light so as to project a distorted image on said sensing field, so that said distorted image is sensible at said image sensor substantially with the image resolution level.

2. An endoscope according to claim 1, wherein said image distorter comprises an image splitter operable to split said image into two part images.

3. An endoscope according to claim 2 wherein said image sensor comprises two sensor parts, each separately arranged along longitudinal walls of said endoscope.

4. An endoscope according to claim 3, wherein said two parts are arranged in successive lengths along opposite longitudinal walls of said endoscope.

5. An endoscope according to claim 1, wherein said distorter is an astigmatic image distorter.

6. An endoscope according to claim 1, wherein said image distorter is an image rectangulator such that the distorted image is a rectangulated image.

7. An endoscope according to claim 6, wherein said sensing field has a rectangular shape substantially complementary to the rectangulated image, as projected by the image distorter.

8. An endoscope according to claim 1, wherein said image distorter comprises at least one lens.

9. An endoscope according to claim 8, wherein said image distorter comprises at least one image-distorting mirror.

10. An endoscope according to claim 9, wherein said image distorter comprises at least a second image-distorting mirror.

11. An endoscope according to claim 8, wherein said image distorter comprises optical fibers to guide image light substantially from said lens to said image sensor.

12. An endoscope according to claim 8, wherein said image distorter comprises a second lens.

13. An endoscope according to claim 8, wherein said image distorter comprises at least one flat optical plate.

14. An endoscope according to claim 1, further comprising at least one light source for illuminating an object, said light source being controllable to flash at predetermined times.

15. An endoscope according to claim 14 further comprising a second light source, said first and said second light sources each separately controllable to flash.

16. An endoscope according to claim 15, wherein said first light source is a white light source and said second light source is an a source of invisible light radiation.

17. An endoscope according to claim 16, wherein said second light source is an IR source.

18. An endoscope according to claim 17, one light source comprising light having a first spectral response and the other light source comprising light having a second spectral response.

19. An endoscope according to claim 16, wherein said second light source is a UV light source.

20. An endoscope according to claim 15, one light source being a right side light source for illuminating an object from a first side and the other light source being a left side light source for illuminating said object from a second side.

21. An endoscope according to claim 20 further comprising color filters associated with said light gatherer to separate light from said image into right and left images to be fed to respective right and left distance measurers to obtain right and left distance measurements for construction of a three-dimensional image.

22. An endoscope according to claim 20, said light sources being configured to flash alternately.

23. An endoscope according to claim 20, further comprising a relative brightness measurer for obtaining relative brightnesses of points of said object using respective right and left illumination sources, thereby to deduce 3 dimensional distance information of said object for use in construction of a 3 dimensional image thereof.

24. An endoscope according to claim 14, further comprising a image gatherer and a second image sensor.

25. An endoscope according to claim 24, wherein one of said image sensors is a color image sensor and a second of said image sensors is a monochrome image sensor.

26. An endoscope according to claim 24, wherein said first and said second image sensors are arranged back to back longitudinally within said endoscope.

27. An endoscope according to claim 24, wherein said first and said second image sensors are arranged successively longitudinally along said endoscope.

28. An endoscope according to claim 27, wherein said first and said second image sensors are arranged along a longitudinal wall of said endoscope.

29. An endoscope according to claim 1, comprising a brightness averager operable to identify brightness differentials due to variations in distances from said endoscope of objects being illuminated, and substantially to cancel said brightness differentials.

30. An endoscope according to claim 29, further comprising at least one illumination source for illuminating an object with controllable width light pulses and wherein said brightness averager is operable to cancel said brightness differentials by controlling said widths.

31. An endoscope according to claim 1, having at least two controllable illumination sources, one illumination source for emitting visible light to produce a visible spectrum image and one illumination source for emitting invisible light to produce a corresponding spectral image, said endoscope being controllable to produce desired ratios of visible and invisible corresponding spectral images.

32. An endoscope according to claim 1, wherein said sensing field has a first field dimension and a second field dimension, the first field dimension being less than or equal to the second field dimension, and wherein said at least one image sensor is disposed within said endoscope so that the first field dimension has a dimensional component transverse to the endoscope's longitudinal dimension.

33. An endoscope according to claim 32, wherein the first field dimension is less than or equal to the endoscope's diameter.

34. An endoscope according to claim 32, wherein said at least one image sensor is disposed within said endoscope so that the second field dimension has a dimensional component along or parallel to the endoscope's longitudinal dimension.

35. An endoscope according to claim 32, wherein said at least one image sensor is disposed within said endoscope so that the second field dimension has a dimensional component other than along or parallel to the endoscope's longitudinal dimension.

36. An endoscope according to claim 1, wherein said at least one image distorter is arranged so as to project the distorted image substantially over the sensing field.

37. An endoscope system, the system comprising:
an endoscope and image processor; said endoscope gathering light, and having a longitudinal dimension along which the endoscope has a tubular cross-section with an internal diameter, the endoscope including
at least one image sensor disposed within the endoscope at a location characterized by the cross-section, and having a rectangular sensing field, the rectangular sensing field having an image resolution level and having a maximum diagonal dimension that is greater than the endoscope's internal diameter, and
at least one image distorter, said at least one image distorter distorting the gathered light so as to project a distorted image on said sensing field, so that the distorted image is sensible at said image sensor with substantial retention of the image resolution level; and said image processor operable for processing image output of said endoscope.

38. An endoscope system according to claim 37, wherein said image processor is a motion video processor operable to produce motion video from said image output.

39. An endoscope system according to claim 37, wherein said image processor comprises a 3D modeler for generating a 3D model from said image output.

40. An endoscope system according to claim 39, wherein said image processor further comprises a 3D imager operable to generate a stereoscopic display from said 3D model.

41. An endoscope system according to claim 37, further comprising an image recorder for recording imaging.

42. An endoscope system according to claim 37, further comprising a control and display communication link for remote control and remote viewing of said system.

43. An endoscope system according to claim 37, wherein said image distorter comprises an image splitter operable to split said image into two part images.

44. An endoscope system according to claim 37, wherein said image sensor comprises two sensor parts, each separately arranged along longitudinal walls of said endoscope.

45. An endoscope system according to claim 44, wherein said two parts are arranged in successive lengths along opposite longitudinal walls of said endoscope.

46. An endoscope system according to claim 37, wherein said image distorter is an astigmatic image distorter.

47. An endoscope system according to claim 37, wherein said image distorter is an image rectangulator such that the distorted image is a rectangulated image, and wherein said sensing field has a rectangular shape substantially complementary to the rectangulated image, as projected on said sensing field.

48. An endoscope system according to claim 47, wherein said image distorter comprises at least one flat optical plate.

49. An endoscope system according to claim 48, further comprising a second light source, said first and said second light sources each separately controllable to flash.

50. An endoscope system according to claim 49, one light source being a right side light source for illuminating an object from a first side and the other light source being a left side light source for illuminating said object from a second side.

51. An endoscope system according to claim 50, one light source comprising light of a first spectral response and the other light source comprising light of a second spectral response.

52. An endoscope system according to claim 51, further comprising color filters associated with said light gatherer to separate light from said image into right and left images to be fed to respective right and left distance measurers to obtain right and left distance measurements for construction of a three-dimensional image.

53. An endoscope system according to claim 51, said light sources being configured to flash alternately.

54. An endoscope system according to claim 51, said light sources being configured to flash simultaneously.

55. An endoscope system according to claim 51, further comprising a relative brightness measurer for obtaining relative brightnesses of points of said object using respective right and left illumination sources, thereby to deduce 3 dimensional distance information of said object for use in construction of a 3 dimensional image thereof.

56. An endoscope system according to claim 55, wherein said first and said second image sensors are arranged back to back longitudinally within said endoscope.

57. An endoscope system according to claim 56, wherein said first and said second image sensors are arranged along a longitudinal wall of said endoscope.

58. An endoscope system according to claim 55, wherein said first and said second image sensors are arranged successively longitudinally along said endoscope.

59. An endoscope system according to claim 37, further comprising at least one light source for illuminating an object.

60. An endoscope system according to claim 59, wherein said first light source is a white light source and said second light source is an invisible light source.

61. An endoscope system according to claim 59, further comprising a second image gatherer and a second image sensor.

62. An endoscope system according to claim 37, wherein said image distorter comprises at least one lens.

63. An endoscope system according to claim 62, wherein said image distorter comprises at least one image-distorting mirror.

64. An endoscope according to claim 62, wherein said image distorter comprises optical fibers to guide image light substantially from said lens to said image sensor.

65. An endoscope system according to claim 62, wherein said image distorter comprises a second lens.

66. An endoscope system according to claim 62, wherein said image distorter comprises at least a second image-distorting mirror.

67. An endoscope system according to claim 37, comprising a brightness averager operable to identify brightness differentials due to variations in distances from said endoscope of objects being illuminated, and substantially to reduce said brightness differentials.

68. An endoscope having a longitudinal dimension along which the endoscope has a tubular cross-section with an internal diameter, the endoscope gathering an optical image via light of a field of view, said optical image characterized by resolution and dynamic range parameters corresponding to proper image acquisition thereof, the endoscope comprising:

an image distorter and an image sensor, the image sensor having a substantially rectangular sensing field comprising a sensing surface, the sensing surface having a sensing area supporting resolution and dynamic range substantially compatible with the optical image's resolution and dynamic range parameters, and the image sensor being disposed within said endoscope at a location characterized by the cross-section so that the sensing surface has se a dimensional component along or parallel to the endoscope's longitudinal dimension, and the image distorter distorting the gathered light substantially into a rectangular shape and projecting such distorted light to the image sensor, so as to form an image on said sensing field, the formed image having an area larger than the endoscope's cross-sectional area as determined by the internal diameter.

69. An endoscope according to claim 68, further comprising a contrast equalizer for compensating for high contrasts differences due to differential distances of objects in said field of view.

70. An endoscope according to claim 68, comprising two illumination sources for illuminating said field of view.

71. An endoscope according to claim 70, said illumination sources being controllable to illuminate alternately, and said image sensor being controllable to gather images in synchronization with said illumination sources thereby to obtain independently illuminated images.

72. An endoscope according to claim 70, each illumination source having a different predetermined spectral response.

73. An endoscope according to claim 72, said image sensor comprising pixels, each pixel being responsive to one of said predetermined spectral responses.

74. An endoscope according to claim 68, said image sensor comprising a plurality of pixels responsive to white light.

75. An endoscope according to claim 68, said image sensor comprising a plurality of pixels responsive to different wavelengths of light.

76. An endoscope according to claim 75, said wavelengths comprising at least three of red light, green light, blue light and infra-red light.

77. An endoscope according to claim 68, further comprising a second image sensor for forming a second image from light obtained from said field of view.

78. An endoscope according to claim 77, wherein one of said image sensors is a color sensor and a second of said image sensors is a monochrome sensor.

79. An endoscope according to claim 77, said second image sensor being placed in back to back relationship with said first image sensor over a longitudinal axis of said endoscope.

80. An endoscope according to claim 77, said second image sensor being placed in end to end relationship with said first image sensor along a longitudinal wall of said endoscope.

81. An endoscope according to claim 77, said second image sensor being placed across from said first image sensor on facing internal longitudinal walls of said endoscope.

82. An endoscope according to claim 68, wherein said image distorter comprises a plurality of optical fibers for guiding parts of a received image to said image sensor.

83. An endoscope according to claim 68, wherein said sensing field has a first field dimension and a second field dimension, the first field dimension being less than or equal to the second field dimension, and wherein said at least one image sensor is disposed within said endoscope so that the first field dimension has a dimensional component transverse to the endoscope's longitudinal dimension.

84. An endoscope according to claim 83, wherein the first field dimension is less than or equal to the endoscope's diameter.

* * * * *